United States Patent
Von Chamier et al.

(10) Patent No.: US 6,797,007 B1
(45) Date of Patent: Sep. 28, 2004

(54) PRESS FIT CONNECTION BETWEEN PROSTHESIS COMPONENTS OF JOINT PROSTHESES

(75) Inventors: Wilfried Von Chamier, Stuttgart (DE); Ernst Hoch, Notzingen (DE)

(73) Assignee: Ceramtec AG Innovative Ceramic Engineering, Plochingen (DE)

( * ) Notice: Subject to any disclaimer, the term of this patent is extended or adjusted under 35 U.S.C. 154(b) by 444 days.

(21) Appl. No.: 09/646,703

(22) PCT Filed: Mar. 25, 1999

(86) PCT No.: PCT/EP99/02245

§ 371 (c)(1),
(2), (4) Date: Nov. 27, 2000

(87) PCT Pub. No.: WO99/48446

PCT Pub. Date: Sep. 30, 1999

(30) Foreign Application Priority Data

Mar. 25, 1998 (DE) .......................................... 198 13 074

(51) Int. Cl.⁷ .............................................. A61F 2/32
(52) U.S. Cl. ................................................ 623/22.45
(58) Field of Search ......................... 623/22.45, 22.17, 623/22.19, 22.24, 22.26, 22.28, 22.3, 22.4, 23.36, 23.4, 23.51, 23.11, 23.12, 23.13, 23.14

(56) References Cited

U.S. PATENT DOCUMENTS

| | | | |
|---|---|---|---|
| 3,720,996 A | * 3/1973 | Tschermak ................ 29/527.1 |
| 3,855,638 A | * 12/1974 | Pilliar ................................ 3/1 |
| 4,032,994 A | * 7/1977 | Frey ............................. 3/1.91 |
| 4,058,856 A | * 11/1977 | Doerre et al. ................ 3/1.91 |
| 4,170,794 A | * 10/1979 | Zeibig et al. ................ 3/1.91 |
| 4,365,356 A | * 12/1982 | Broemer et al. .............. 3/1.9 |
| 4,479,271 A | * 10/1984 | Bolesky et al. ............. 3/1.91 |
| 4,908,034 A | 3/1990 | Weightman |
| 4,921,500 A | * 5/1990 | Averill et al. ................ 623/22 |
| 4,997,445 A | * 3/1991 | Hodorek ...................... 623/16 |
| 5,066,304 A | * 11/1991 | Crowninshield et al. ...... 623/22 |
| 5,108,025 A | * 4/1992 | Kang et al. ................ 228/122 |
| 5,258,033 A | * 11/1993 | Lawes et al. ................ 623/23 |
| 5,258,098 A | * 11/1993 | Wagner et al. ............. 156/645 |

(List continued on next page.)

FOREIGN PATENT DOCUMENTS

| | | |
|---|---|---|
| CH | 676922 | 2/1989 |
| DE | 19529988 | 8/1995 |
| DE | 19537676 | 4/1997 |
| DE | 19615802 | 10/1997 |
| DE | 19616058 | 10/1997 |
| DE | 19640745 | 1/1998 |
| EP | 385572 | 9/1990 |
| FR | 2644691 | 9/1990 |

*Primary Examiner*—Bruce Snow
*Assistant Examiner*—Cheryl Miller
(74) *Attorney, Agent, or Firm*—Antonelli, Terry, Stout & Kraus, LLP

(57) ABSTRACT

Joint prostheses which have one joint partner configured as a socket and the other joint partner configured as a ball head generally consist of two components. The socket is comprised of a metallic outer cup in which an insertion cup made of ceramic material or of a biocompatible plastic is inserted. The shaft has a peg, the so-called cone, on which a ball head is placed. The press fit connection, especially so-called conical pressing, is used as a connection technique between the respective components. Stress can result in a relative movement between the components, thus leading to a wear-related loosening of the connection thereof. In order to solve this problem, the invention provides that, from the prosthetic components (2, 3), the component (3) made of ceramic or plastic fitted with a covering (6), said covering being made of a biocompatible metal or of a biocompatible metal alloy, on the pressing surface (7) thereof via which said component (3) is connected to the metal component (2).

9 Claims, 3 Drawing Sheets

U.S. PATENT DOCUMENTS

| | | | | |
|---|---|---|---|---|
| 5,362,311 A | * | 11/1994 | Amino et al. | 623/22 |
| 5,365,661 A | * | 11/1994 | Mizuno et al. | 29/889.21 |
| 5,456,723 A | * | 10/1995 | Steinemann et al. | 623/16 |
| 5,462,362 A | * | 10/1995 | Yuhta et al. | 384/13 |
| 5,609,647 A | * | 3/1997 | Kalberer et al. | 623/22 |
| 5,826,586 A | * | 10/1998 | Mishra et al. | 128/898 |
| 5,904,720 A | * | 5/1999 | Farrar et al. | 623/22 |
| 6,008,432 A | * | 12/1999 | Taylor | 623/16 |
| 6,045,581 A | * | 4/2000 | Burkinshaw | 623/18 |
| 6,087,553 A | * | 7/2000 | Cohen et al. | 623/16 |
| 6,312,473 B1 | * | 11/2001 | Oshida | 623/23.55 |

* cited by examiner

PRESS FIT CONNECTION BETWEEN PROSTHESIS COMPONENTS OF JOINT PROSTHESES

BACKGROUND OF THE INVENTION

The invention relates to a press-fit connection between prosthesis components of joint prostheses in accordance with the preamble of the first claim.

Joint prostheses, in which one joint partner is formed as a socket and the other joint partner is formed as a spherical head which is rotatably mounted in the socket, are known in particular as shoulder-joint and hip-joint prostheses. These prostheses, as a rule, are built up in a modular fashion. Hip-joint endoprostheses, for example, consist of the socket, which is inserted into the hip bone, and of the shaft, which is inserted into the femur. The socket consists, as a rule, of a metallic outer shell into which a shell insert made of ceramic material or a biocompatible plastics material is inserted. A press-fit connection is used here as the connecting technique. A press-fit connection is known, for example, from DE 196 11 248A1. The shaft has a peg, the so-called cone, onto which the spherical head is slipped. In the case of the modularly constructed endoprostheses, implant components are connected together that are made of different materials and are of different sizes for the purposes of adaptation to the physique of the patient. For example, spherical heads made of a cobalt-chromium alloy or made of an aluminium-oxide ceramic material are slipped onto a cone made of titanium. The press-fit connection, in particular conical pressing, is also used here as the connecting technique between metallic or ceramic spherical heads and the cone. In this connection, the spherical head which has a conical bore is placed upon the cone. After the spherical head has been slipped onto the cone, fixing is effected by hitting the spherical head.

As is known from the publication "Das Prinzip der Konus-Steckverbindung für keramische Kugelköpfe bei Hüftendoprothesen" by G. Willmann, Mat-wiss. u. Werkstofftech. 24, 315–319 (1993), all ceramic materials are brittle, that is to say, they are sensitive to non-areally introduced loads, that is, stress concentrations. The contact surfaces between the bore in the ceramic ball and the surface of the cone must be matched to each other in an optimum manner. The percentage bearing area proportion of the surfaces that is provided must be the maximum possible. It has been possible to achieve this by making extremely high demands with respect to the dimensional tolerances of the bore and of the metal cone. However, since that cannot be realized technically and is not expedient economically, the potential of the plastic deformability of the metals is exploited by structuring the surface of the metallic cone. For example, the surface is roughened to a great extent or is provided with a specific structure, for example it is provided with a groove. If the spherical head is now slipped onto the metallic cone, the structured surface is deformed and the percentage bearing area proportion of the surfaces is increased. As a result, the stress concentration is minimized and in addition the friction is increased so the protection against torsion is also improved. The greater the roughness-height that lies in the micrometer range is, the higher the tolerable breaking load is. Since, however, the ceramic material, is harder than the metallic material of the cone, in particular in the case of load-related relative movements between the cone and the spherical head, it is possible that abrasion will occur on the surface of the cone and loosening of the connection will take place. Manifestations of wear as a result of relative movements are also possible in the case of joint sockets where the shell insert is held in the outer shell by means of a press-fit.

SUMMARY OF THE INVENTION

The object of the present invention is to propose an improved press-fit connection between the prosthesis components of joint prosthesis, i.e., between a metallic component which is anchored in the bone and a ceramic or biocompatible plastic component forming a friction partner of the joint.

The object is achieved with, by providing the ceramic or biocompatible plastic component with a covering made from a biocompatible metal or biocompatible metal alloy on its pressing surface by way of which it is connected to the metallic component.

The covering in accordance with the invention made from a biocompatible metal or a biocompatible metal alloy on one of the pressing surfaces of the components, the inner surface of the conical bore of the spherical head or the outer cone section of the shell insert respectively, acts as an adhesion promoter between the spherical head and the cone of the shaft or the shell insert and the outer shell of the joint socket respectively. The covering can be produced to any thickness that is desired. Electrolytic deposition or deposition out of the gas phase (sputtering) is possible. A preferred method of application is spraying, with plasma-spraying being particularly suitable for spraying metals or metal alloys that have high melting points. Plasma-spraying presents the possibility of being able to produce a coating to the required thickness by adjusting the distance of the flame and the temperature of the flame. What is important in the case of all the coating methods and coating materials is that there is good adhesion between the coating material and the surface of the prosthesis components made from ceramic or plastics material. This adhesion can be effected by means of a form of mechanical clamping in the rough surface of the ceramic material or plastics material or by connecting the material which is applied to the corresponding material in the boundary layer. This is possible in particular when plasma-spraying metallic materials that have high melting points, for example in the case of titanium alloys.

When pressing the spherical head onto the cone and also when pressing the shell insert into the outer shell, in addition to the frictional adhesion as a result of the great pressure on the covering, it is possible for a connection to be established between the material of the covering and the metallic material of the pressing surface of the cone or the outer shell respectively, for example in the form of a so-called cold-weld, by means of which the adhesion of the two components can be increased.

The adhesion of the prosthesis components made from ceramic material or plastics material to their metal partners, the adhesion of a spherical head to a cone and also of a shell insert to an outer shell, is advantageously increased owing to the fact that the covering has a rough surface. When a spherical head is pressed onto the cone of a shaft as well as when a shell insert is pressed into an outer shell, the tips of the rough surface of the covering are levelled, whereby a large percentage bearing area is produced for the frictional adhesion. The surface of the covering may already be rough on account of the method of application itself, for example plasma spraying, yet can also be brought to the desired height of roughness by means of subsequent treatment, for example sand blasting.

A corresponding increase in material develops as a result of the covering in the region of the pressing surfaces, on the lateral surface of the conical bore or the outer cone section respectively. It is therefore advantageous if the dimensions of the prosthesis components in the region of the pressing surfaces are selected with regard to the dimensions with the covering that are required for a press-fit so that the covering can be applied to an optimum thickness and with an optimum roughness-height matched to the respective pairing of components. Moreover, advantageously as a result of the covering on one of the pressing surfaces, the possibility exists of compensating for tolerances or deviations from the straightness and roundness of the cone and conical bore in the spherical head or shell insert and inner cone section in the outer shell, whereby the risk of relative movements under loading as a result of a bad fit is precluded.

Depending on the material, method of application and layer thickness, the covering can have a roughnesses of 20 μm to 90 μm depth. The depths of roughness of the pressing surfaces of the components that are to be connected together by means of adhesive friction have a decisive influence upon, in particular, the breaking load of the ceramic component. With an increasing depth of roughness of the pressing surface of the metallic partner in conventional connections, the breaking load of the ceramic component increases. In order to guarantee a solid and durable fit of the components in accordance with the invention, advantageously, the toughness depth of the covering should, if possible, not drop below substantially 20 μm. With a decreasing roughness depth, the resistance against levelling of the peaks increases and a comparatively high level of force must be used.

A roughness depth of between 60 μm and 90 μm has proved to be particularly advantageous. This is due to the fact that consequently peaks of a sufficient height are provided that are levelled when a spherical head is mechanically pressed onto a cone or when a shell insert is pressed into an outer shell and which, with increasing levelling, result in an increasing percentage bearing area. With an increasing percentage bearing area, the friction and therefore also the security against relative movements, in particular torsion, of the spherical head and cone, or the shell insert and outer shell, increase.

Spherical heads and shell inserts made from ceramic material have proved to be advantageous not just because of their wear resistance. Since ceramic materials do not have any corrosive effect upon metals or metal alloys, they can quite safely be provided with a covering of a biocompatible metal or a biocompatible metal alloy.

Furthermore, it is advantageous if the material of the covering and the material of the pressing surface of the cone or the outer shell correspond. It is known that in the case of implant components made from different materials, for example where a spherical head of cobalt chromium is slipped onto a shaft made from titanium alloys, on account of relative movement between the portions and the presence of the body fluid acting as an electrolyte, so-called fretting corrosion is possible. On account of the micro-movements that occur between the spherical head and cone as a result of the body load, it is possible for detectable abrasion to occur that results in damage to the protective oxide layer of the otherwise biocompatible metals or metal alloys. The so-called fretting corrosion is caused by the resultant galvanic reactions of the different metal components rubbing against each other.

BRIEF DESCRIPTION OF THE DRAWINGS

The invention is explained in greater detail with reference to a hip-joint endoprosthesis as an exemplifying embodiment. In the drawings.

DETAILED DESCRIPTION OF THE PREFERRED EMBODIMENTS

Figure 1:
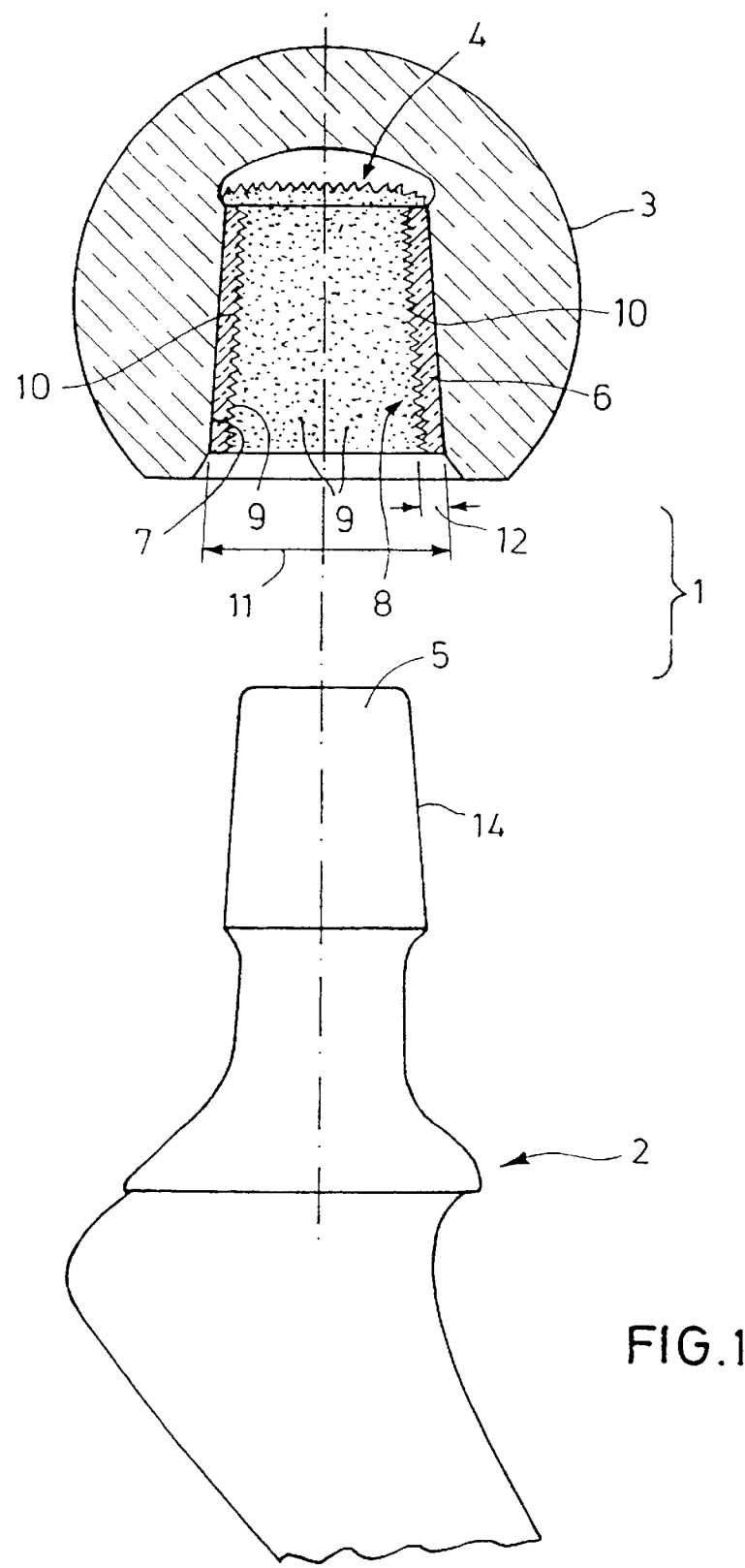
FIG. 1 shows the shaft of a hip-joint endoprosthesis and a spherical head with a conical bore provided with the covering in accordance with the invention.

In FIG. 1 a shaft 2 and an associated spherical head 3 of ceramic material, for example of aluminium oxide, of a hip-joint endoprosthesis 1 are shown on an enlarged scale. The spherical head 3 has a conical bore 4 to take up the cone 5 of the shaft 2. The shaft 2 and its cone 5 in the present exemplifying embodiment are made of a titanium alloy, for example TiAl6V4. For the purposes of illustration, the covering 6 in accordance with the invention that is on the lateral surface 7 of the conical bore 4, the pressing surface of the spherical head 3, as can be seen in the half of the spherical head 3 shown in section, is shown on an enlarged scale. The covering 6 consists of the same titanium alloy as the shaft and has been applied by flame spraying. In order to achieve the object that forms the basis of the invention, it suffices if only one of the pressing surfaces, here the lateral surface 7 of the conical bore 4, is provided with the covering 6.

The rough surface 8 of the covering 6, produced by means of the application method, flame spraying, can be seen clearly. The height of roughness $R_1$ preferably lies between 60 μm and 90 μm. When the spherical head 3 is pressed onto the cone 5, the tips 9 are pressed in by means of the pressing surface 14 and fill up the valleys 10. As a result, the percentage bearing area in the covering 6 of the pressing surface 7 of the spherical head 3 is increased considerably.

So that the spherical head 3 occupies the correct position after it has been pressed onto the cone 5, the diameter 11 of the conical bore 4 and the layer thickness 12 of the covering 6 are matched in respect of each other in such a way that a covering 6 with a predeterminable height of roughness and thickness 12 can be applied to the pressing surface 7, so that the pressing force required to hold the components together is achieved.

Figure 2:
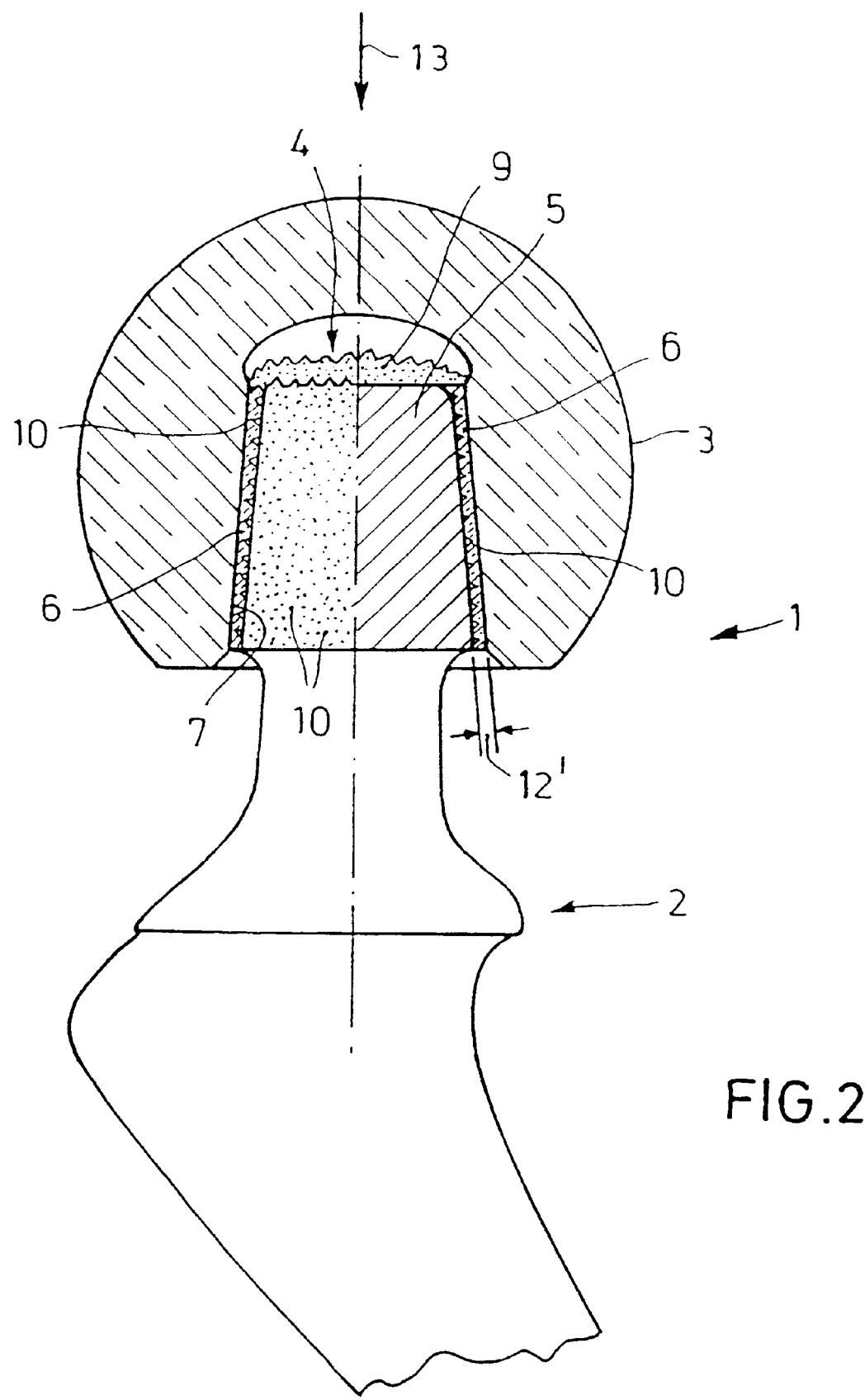
FIG. 2 shows the shaft that is ready for implantation with the spherical head slipped onto the cone.

FIG. 2 shows the spherical head 3 and the shaft 2 in the assembled state. The spherical head 3 has been pressed onto the cone 5 in the direction of arrow 13, for example by being tapped by a hammer. In this connection, the peaks 9 (FIG. 1) were levelled when sliding over the pressing surface 14 and the covering 6 was compressed to the thickness 12', as can be seen in the view and in the section of the covering 6 in FIG. 2. The percentage bearing area, which, in contrast with FIG. 1, is shown in white in FIG. 2 in the view of the levelled covering, is increased and evened out, whereby the stress concentrations, which otherwise occur as a result of the non-areally introduced loads, are reduced to a minimum. In addition to the comparatively large amount of friction that is occasioned thereby, the protection against torsion of the two components is increased. The black areas 10 in the view of the covering 6 represent the valleys that remain and which are not yet filled up. The metallurgical connections which result on account of the high surface pressure on the covering 6 at the boundary surface between the pressing surface 14 of the cone 5 and the covering 6 and which contribute to the increase in adhesion are not shown.

Figure 3:
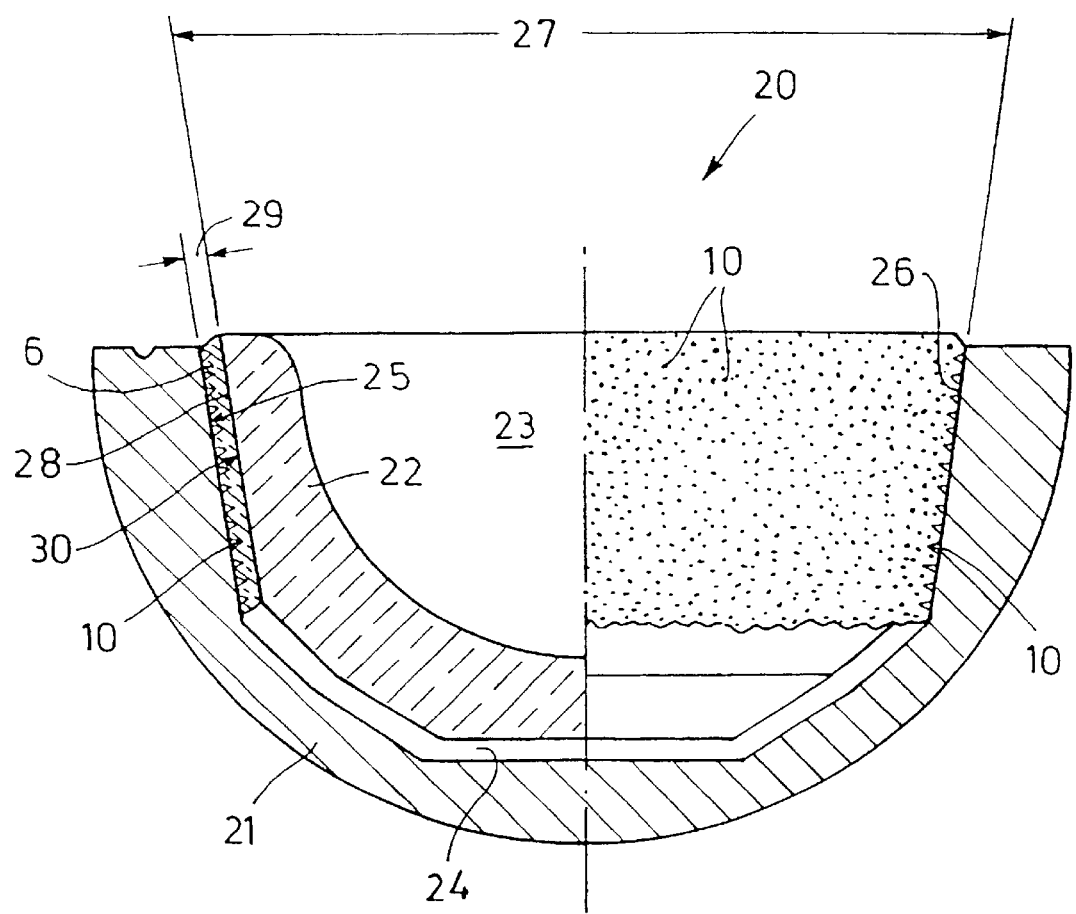
FIG. 3 shows a section through a joint socket, into the outer shell of which a shell insert provided with the covering in accordance with the invention is pressed.

A prosthetic joint socket 20 is shown in section in FIG. 3. It is formed by an outer shell 21 and a shell insert 22 which is inserted therein. The covering and its features are provided with the same reference numerals as in the previous exemplifying embodiment. The outer shell 21 consists of a biocompatible metal, whilst the shell insert 22 can be made of ceramic material or a biocompatible plastics material. The hollow space 23 in the shell insert 22 is used to take up the spherical head of the joint (not shown here, see FIGS. 1 and 2).

Whilst the outer contour of the outer shell 21 in the present exemplifying embodiment has the shape of a ball, the hollow space 24 provided to take up the shell insert 22 has a conically shaped portion 25. Its lateral surface constitutes the pressing surface 26 for the shell insert 22 which rests against the outer shell 21 just in this region of the inner wall.

So that the shell insert 22 occupies the correct position after being pressed into the conically shaped recess 25 of the outer shell 21, the diameter 27 of the outer cone section 30 of the shell insert 22 is to be dimensioned in such a way that a covering 6 can be applied to the pressing surface 28 that is of the thickness and predeterminable height of roughness that the pressing force that is required to hold the components together is achieved thereby.

The assembled state of the outer shell 21 and the shell insert 22 shows that the rough surface of the covering 6 has been substantially levelled by the pressing surface 26 of the outer shell 21 and the covering 6 has been compressed in respect of the thickness 29. In the view of the covering 6, as in FIG. 2 of the previous exemplifying embodiment, the bearing area proportion of the covering 6 is shown in white. The black areas 10 represent the valleys that remain. As the view of the levelled covering 6 shows, a large, uniform bearing area proportion is achieved for the press-fit connection of the outer shell 21 and shell insert 22.

What is claimed is:

1. A joint prostheses, comprising a first component comprising a metallic material to be anchored in a bone and a second component forming a friction partner of the joint prosthesis and comprising a ceramic material or a biocompatible plastics material having a clamp surface that is press-fit to the first component to form a press-fit connection, wherein the second component is provided with a coating made from a biocompatible metal or a biocompatible metal alloy on the clamp surface, the coating having a rough surface in which a peak to valley height is sufficient to produce the press-fit connection upon press-fitting the first component and the second component.

2. The joint prosthesis according to claim 1, wherein the dimensions of the first and second components in the region of the press-fit connection are selected with regard to the dimensions with the coating that are required for the press-fit so that the coating can be applied to an optimum thickness and with an optimum roughness-height matched to the first and second components.

3. The joint prosthesis according to claim 1, wherein the peak to valley height of the coating lies between 20 $\mu$m and 90 $\mu$m.

4. The joint prosthesis according to claim 3, wherein the peak to valley height of the coating lies between 60 $\mu$m and 90 $\mu$m.

5. The joint prosthesis according to claim 1, wherein the material of the coating corresponds to the material of the first component.

6. Press-fit connection according to claim 1, wherein the coating is provided on the clamping surface of the second component by spray coating.

7. A method for forming a joint prosthesis, comprising:

providing a first component comprising a metallic material to be anchored in a bone;

providing a second component forming a friction partner of the joint prosthesis and comprising a ceramic material or biocompatible plastics material having a clamp surface;

forming a coating of a biocompatible metal or a biocompatible metal alloy on the clamp surface, the coating having a rough surface; and press-fitting the first component to the clamp surface of the second component, a peak to valley height of the rough surface of the coating on the clamp surface being sufficient to produce a press-fit connection between the first and second components.

8. The method according to claim 7, wherein the coating is formed by spray coating.

9. The method according to claim 7, wherein the coating is formed by plasma spray coating.

* * * * *